United States Patent [19]

Sarfarazi

[11] Patent Number: 5,304,561

[45] Date of Patent: Apr. 19, 1994

[54] NEW CONCEPT IN GLAUCOMA TREATMENT

[76] Inventor: Faezeh Sarfarazi, 25 Wiswall Rd., Newton Center, Mass. 02159

[21] Appl. No.: 919,597

[22] Filed: Jul. 24, 1992

[51] Int. Cl.$^5$ .............................................. A61K 31/505
[52] U.S. Cl. .................................. 514/274; 514/912; 514/913
[58] Field of Search ...................... 514/274, 912, 913

[56] References Cited

PUBLICATIONS

Biosis Abstract of American Journal of Ophthamology 109(4) 1990.

*Primary Examiner*—Zohreh A. Fay
*Attorney, Agent, or Firm*—Ellen C. Childress

[57] ABSTRACT

A method and materials for stimulating healing of denuded areas in trabecular meshwork cells is disclosed which may be used to treat glaucoma.

9 Claims, 22 Drawing Sheets

NEW CONCEPT IN GLAUCOMA TREATMENT

FIELD OF THE INVENTION

This invention pertains to the treatment of glaucoma.

BACKGROUND OF THE INVENTION

Since ancient times, glaucoma has been known as an incurable disease. Glaucoma is a disease of the eye marked by increased pressure within the eyeball, damage to the optic disc, and gradual loss of vision. Normally, aqueous humor, which supplies nutrients to the lens and cornea and maintains normal intraocular pressure, is produced in the ciliary process. The aqueous humor circulates from the posterior chamber through the pupil and into the anterior chamber. It then drains through and is filtered by the trabecular meshwork, then through Schlemm's Canal and from there through the aqueous veins into the venous system. Elevated intraocular pressure most often results from increased resistance to the normal outflow of aqueous humor from the eye, however, on rare occasions, it is caused by hypersecretion of aqueous humor.

Open angle glaucoma, the most common form of glaucoma increases in frequency and severity with age. Many studies have been done to define the cause of glaucoma. According to these studies, resistance to the aqueous outflow increases and rate of aqueous production decreases with age. It has been suspected for many years that age related changes in trabecular meshwork are responsible for obstruction of aqueous humor outflow. It has been shown that a continuous decrease in trabecular meshwork cellularity occurs throughout life. When cells are lost, remaining cells may stretch, rather than divide to fill gaps. Eventually the trabecular meshwork cell population could become too small to cover the trabeculae. Trabecular meshwork cells are also located around and support the Canal. Loss of cells in the endothelium of Schlemm's canal may be important because resistance in the canal could be reduced initiating a cycle of increased flow and further breakdown. It has been suggested that increase resistance to aqueous outflow may result from compression of the Schlemm's canal, which has been shown experimentally to partially collapse at elevated intraocular pressure. Loss of trabecular meshwork cells would reduce their flow producing action, allow material to deposit in the canal, and contribute to collapse of the canal.

Age related changes in the trabecular extracellular matrix cause increases and accumulations in fibronectin and other extracellular glycoprotein in the drainage pathway of human eyes that may contribute to increased outflow resistance.

Current medication for glaucoma treatment seeks to reduce inflow or increase outflow of the aqueous humor without directing activities of trabecular meshwork cells. Such agents as beta blockers and other anti-hypertensive agents which reduce the amount of aqueous humor and control pressure in the eye.

When such medication no longer controls pressure, filtration surgery in preformed, to relieve the pressure. The trabeculectomy is the most popular technique. In this technique a passageway is made between the subconjunctival space and the anterior chamber by excising the sclera and episclera and then removing the trabeculae. The aqueous humor then passes through the trabeculectomy and goes under the conjunctiva to form a bleb. The success rate of standard filtration surgery ranges between 25–60% in aphakia patients (those without lenses) to 75–95% in phakic eyes. Problems with filtration surgery include scar formation that stops drainage and rarely blockage of trabeculectomy section by other structures in the eye. One means of controlling scarring is the application of 5-Fluorouracil [RN 51-21-8].

For prevention of scarring in the bleb after glaucoma surgery, 5-FU at amounts greater than 100 mg are used. This antimetabolic drug is used daily for a week as a subconjunctival injection of 5–15 mg to eliminate mitosis and migration of conjunctiva and Tenon's capsule fibroblast (mesodermal cells giving rise to connective tissue) toward the filtered bleb. A total dose of 105 mg of 5-FU is employed in treatment of the majority of patients. The threshold concentration for 5-FU toxicity to the cornea in the endothelium lies between 1 and 10 mg/ml for a 4 hour exposure. It is known that 5-FU inhibits fibroblasts.

Uracil is a pyrimidine base occurring in RNA. In some RNAs, especially low molecular weight amino acid transfer RNA of the cytoplasm, hypoxanthine and various methylated bases replace some of the native component. Certain bases (and their nucleosides and nucleotides) not usually occurring in nature act as chemotherapeutic and mutagenic agents, because they are readily incorporated into nucleic acids instead of the native bases. Among them are the uracil analogs 2-thio- and 5-Fluorouracil, 5-Bromouracil, and the guanine analogs 8-azaguanine and 2,6-diamanopurine. As a result of incorporation into the RNA, modified proteins are formed. This alteration becomes manifest soon after introduction of the analog and is relieved after its removal and replacement by the native base.

The alterations produced in this way vary even for any one organism. For the inducible beta galactosidease, they lead to a loss of activity; for the repressible alkaline phosphatase, the protein is still active but exhibits a different heat stability; and for one group of phage mutants in a restricted host, it may actually lead to the formation of a functional, rather than an inactive protein. Thus the action of the 5-Fluorouracil is unpredictable. Under certain unusual circumstances, the result of treatment with 5-Fluorouracil results in an altered protein which may sufficiently resemble that of the native type and be produced in sufficient amounts so as to permit function and/or growth.

5-FU is a cytostatic drug with antimetabolitic action which inhibits thymidine synthetase and thus formation of DNA. Present uses of 5-Fluorouracil include anticancer agents and as an antiscarring agent after glaucoma filtration surgery.

Uncontrolled stimulation of mitosis creates cancer. Thus, anticancer drugs are generally antimitotic. It is clear from present literature, that 5-FU, being anticytotic was considered to be inhibitory to cell growth. The anticytotic action of 5-FU appear at higher doses occurs for both mitotic and migratory processes. For treatment of cancer, the 5-FU may be administered orally, by injection, through implants, creams, ointments and drops, depending on the location and type of cancer. Dosages range from 300 to 1000 mg/m2.

Methods of applying 5-Fluorouracil include injections, creams, drops, and implants are described in U.S. Pat. Nos. 4,863,457 and 4,997,652, incorporated herein by reference. To achieve antiscarring activity 5-Fluorouracil is given in dosages far exceeding the 10 ug/ml used in the present invention. Jon Ruderman et al discuss the use of Fluorouracil in "A Prospective, Randomized Study of 5-Fluorouracil and Filtration surgery", Tr. Am. Ophth. Soc. vol. LXXXV, 1987 and "Low-Dose 5-Fluorouracil and Glaucoma Filtration Surgery", Ophthalmic Surgery, vol. 20, No. 5. These studies showed even at low dosages, 5-Fluorouracil provided significantly lower postoperative intraocular pressure.

The inventor is unaware of any suggestion that 5-Fluorouracil can be effective treatment for glaucoma without filtration surgery.

SUMMARY OF THE INVENTION

Cell activity to heal a wound occurs through mitosis (division of the cell) and cell migration. The filtering action of the trabecular meshwork cells is maintained through these mechanisms. When the meshwork filter action is compromised due to cell loss, the meshwork can not act properly and pressure builds in the eye.

Certain compounds, in particular 5-Fluorouracil and 3-Fluorouracil have been found to allow the trabecular meshwork (TM) to reform when given in very low dosages in vitro. Parallel healing in vivo could allow for filtration action to occur and prevent blockage and the resultant intraocular pressure build up. Thus a non-surgical treatment for glaucoma would become available.

It is believed action for rebuilding of the meshwork occurs because the dosage is high enough to prevent division of the meshwork cells but low enough to stimulate migration of cells from a confluent part of the meshwork. The cells migrate to the denuded area of the meshwork and deposit there, reforming the meshwork. Cell culture studies show this unexpected behavior. While other agents may be found for which migratory stimulating dosages exist, the unpredictable nature of proteins resulting from the action of 5-Fluorouracil on RNA may contribute to the healing process.

A pharmaceutical with potential for the nonsurgical treatment of glaucoma is disclosed.

BRIEF DESCRIPTION OF THE PHOTOGRAPHS

DETAILED DESCRIPTION OF THE INVENTION

Preparation and Wounding of Cell Cultures

Figure 1B:
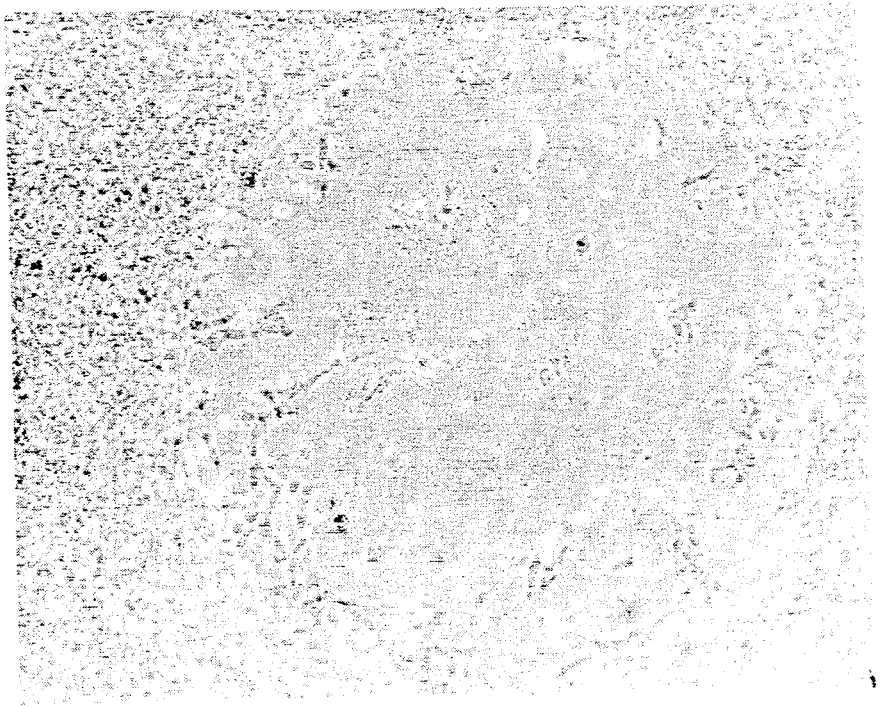
FIG. 1B is a phase micrograph of a wound in TM cultures containing 1 ug/ml colchicine after 10 days (original magnification × 96).

Cell culture and wounding were carried out according to the following procedures.

Cell cultures made from second to fourth passage of calf trabecular cells or human fibroblasts were used. Confluent monolayers of TM cells were grown on glass coverslips in Dulbecco's modified Eagle medium (DMEM, Gibco, Grand Island, N.Y.) containing 10% fetal bovine serum (FBS, Sigma Chem. Corp., St. Louis, Mo.) and either 100 units/ml penicillin, 100 ug/ml streptomycin, 25 ug/ml fungizone or 40 ug/ml gentimicin.

TM cultures were wounded and denuded by the following method, as developed by the inventor. Cultures in the center of the coverslip were wounded with a pipette tip (Fisher Brand Redi Tip) by holding the pipette tip firmly in place with the left hand while turning 180° clockwise with the right hand. The tip was removed after the wounding.

For comparison, human fibroblast cells were cultured and wounded in the same way.

Application of 5-Fluorouracil to cultures

Stock solutions of 5-FU (1 mM prepared in PBS) were diluted with medium. Media with 5 FU concentrations of 0.1–15 ug/ml were added to wounded cultures at serum levels of either 0 or 10%. Wound closure and effects of the 5-FU treatment were monitored by daily examination under a phase microscope. To study long term effects of 5-FU on wound healing, when wound healing was completed, the 5-FU group was further divided into two groups. Medium containing 5 FU was added to one, while medium without 5-FU was added to the second. Wound closure was monitored for six weeks under a light microscope.

The effect of serum on growth on control cultures can be seen as follows. Cell cultures were divided into 2 groups. Group A was grown with serum and Group B was grown without serum. After 24 hours Group A was 75% healed, while Group B was 15% healed. After 48 to 60 hours Group A was almost completely healed, Group B was 20% healed. After 72 hours, Group A was completely healed while Group B was only 40% healed.

Parallel studies using colchicine were conducted.

Staining of the ctyoskeletal and extracellular matrix

To study cytoskeletal and extracellular matrix structures, cultures were fixed with 3.5% formaldehyde for 30 min in dark at room temperature. Fixed cells were then rinsed with PBS (Phosphate buffer solution) for 5 min. Half of the samples were permeablized with Triton X (Solution B) or acetone. Permeablization removes fatty compounds from cells, breaking down membranes thus allowing antibodies to penetrate easily and attach to cytoskeletal components. After permeablization, the coverslip was rinsed 2×5 min. with PBS. The coverslips were then incubated for 1 hr. at 37° C. with primary antibody (Ab), rinsed 3×10 min with PBS and incubated for anther hour with Rhodamin-conjugated or fluorescein-conjugated secondary antibody Ab. For negative controls, the primary Ab was omitted. After washing with PBS the coverslip was mounted on slides with GELTOL (Immunon-Chicago, Ill.) mounting medium and sealed with nail polish. Specimens were studied under a Zeiss microscope under phase and fluorescent optics.

The following Table summarizes immunostaining reagents.

| REAGENTS USED FOR IMMUNOFLUORESCENT STAINING | | |
|---|---|---|
| 1st Antibody | 2nd Antibody | Permeablization |
| Mouse anti-Actin | Anti-mouse IgG | cold MeOH 5 min |
| Mouse anti-Vimentin | Anti-mouse IgG | cold MeOH 5 min |
| Mouse anti-Tubulin | Anti-mouse IgG | cold MeOH 5 min |
| Mouse anti-Desmin | Anti-mouse IgG | cold MeOH 5 min |
| Goat anti-Filamin | Anti-goat IgG | Solution B 1 min |
| Rabbit anti-Spectrin | Anti-rabbit IgG | Solution B 1 min |
| Rabbit anti-a Actin | Anti-rabbit IgG | Solution B 1 min |
| Rabbit anti-Collagen | Anti-rabbit IgG | Solution B 1 min |
| Sheep anti-Fibronectin | Anti-sheep IgG | Solution B 1 min |
| Rabbit anti-Laminin | Anti-rabbit IgG | Solution B 1 min |

Results

A) Colchicine

Figure 1A:
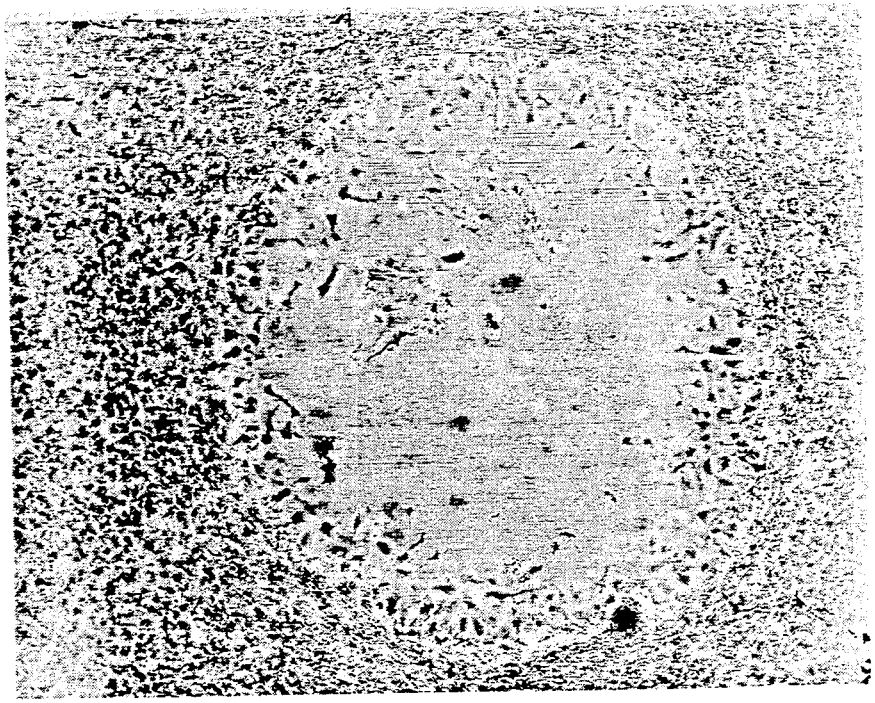
FIG. 1A is a phase micrograph of a wound in TM cultures containing 1 ug/ml colchicine after a few hours (original magnification × 96).

As is evident from FIGS. 1A and 1B colchicine inhibited resurfacing of TM cells, even after 10 days.

B) 5-FU

Figures 2A, 2B:
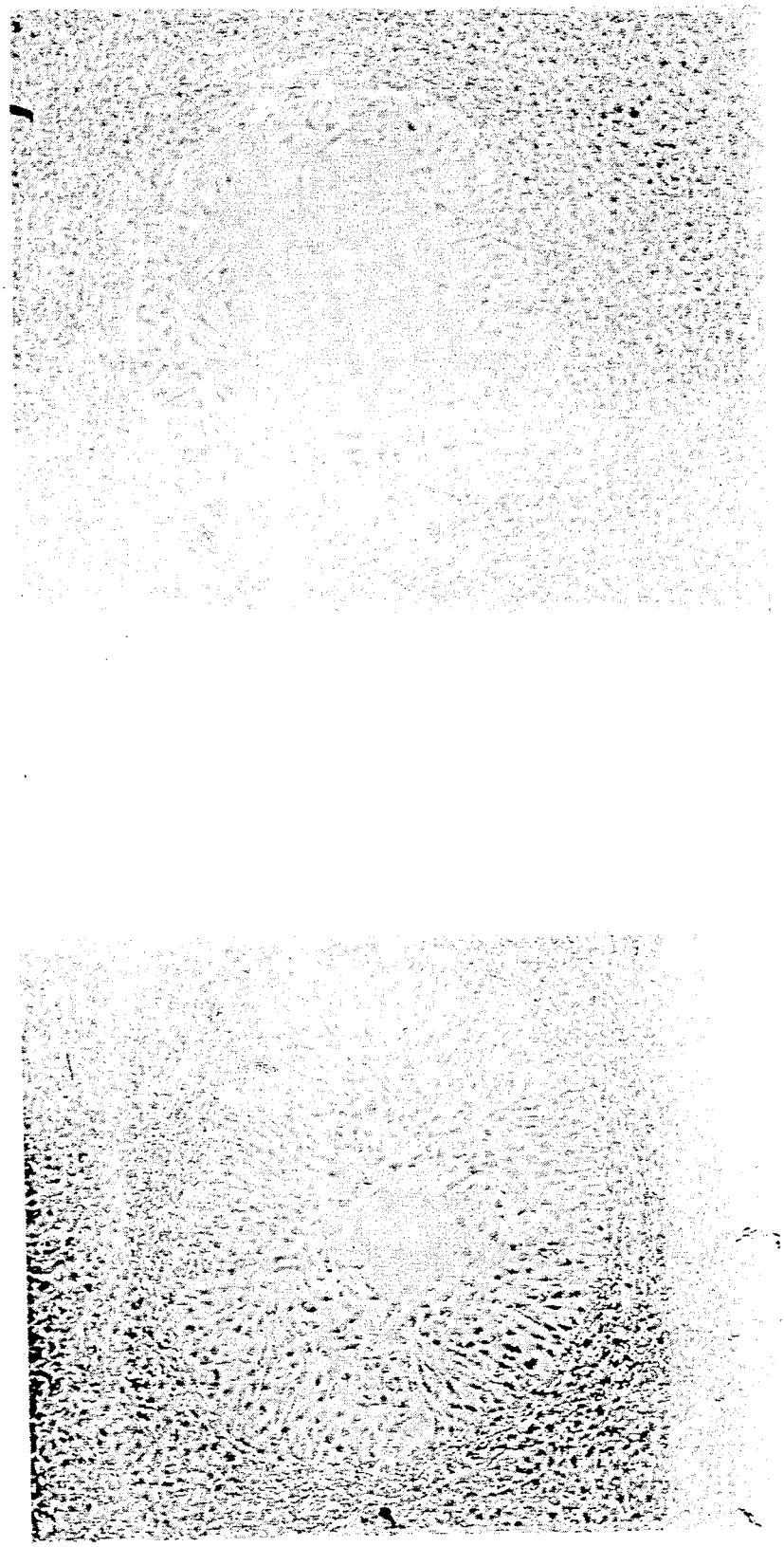
FIG. 2A is a phase micrograph of a wound in TM cultures containing 1 ug/ml 5-FU after 24 hours (original magnification × 86).
FIG. 2B is a phase micrograph of a wound in TM control culture without 5-FU after 24 hours (original magnification × 80).
Figure 2D:
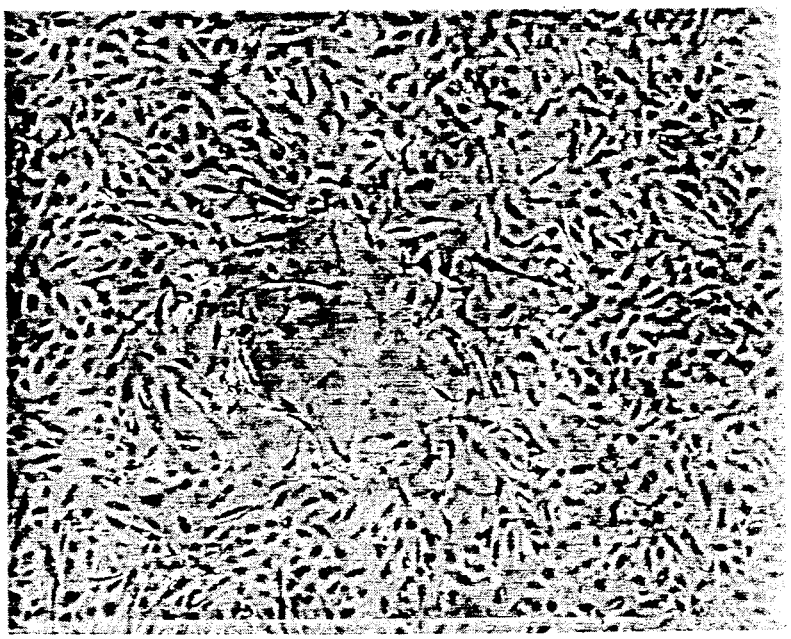
FIG. 2D is a phase micrograph of a wound in TM control culture without 5-FU after 48 hours (original magnification × 80).
Figure 7B:
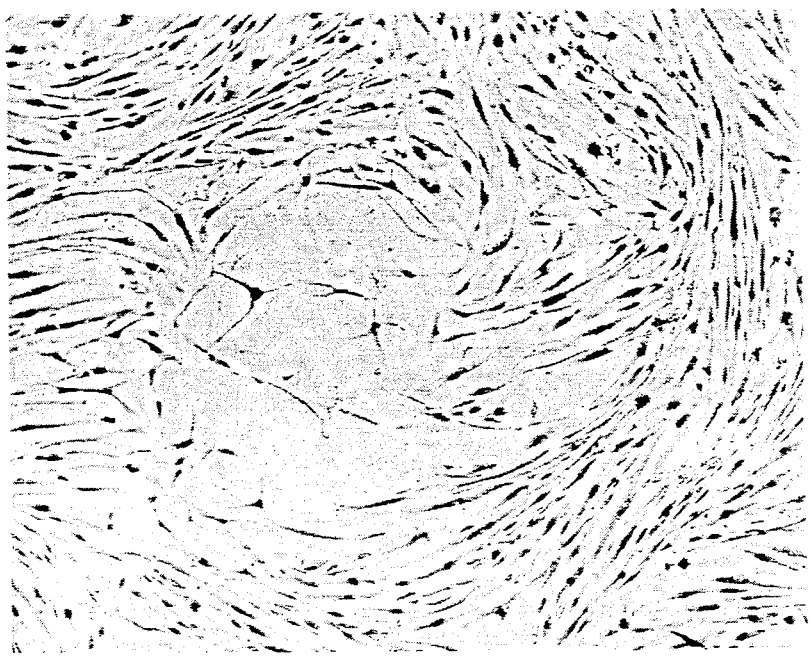
FIG. 7B is a phase micrograph of the wound of 7A after 24 hours (original magnification × 80).
Figure 7A:
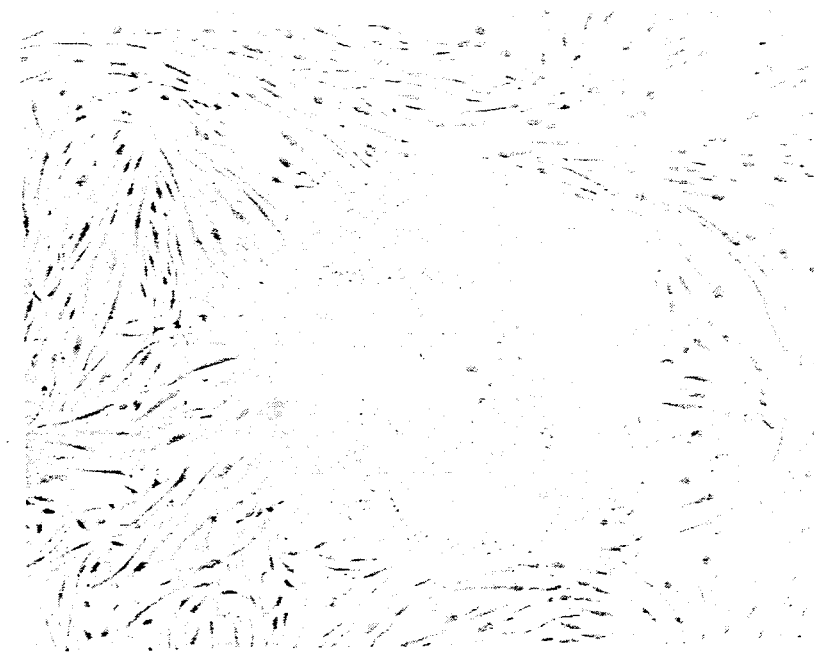
FIG. 7A is a phase micrograph of an initial wound in human fibroblast control cultures (original magnification × 76).

Partial healing of TM control (untreated with 5FU) cultures is observed in 24 hours FIG. 2B. Complete wound healing of control cultures took about 48 to 60 hours for TM (FIG. 2D) and fibroblast cells (FIGS. 7A and 7B). There was no alteration of cellular shape and the edge of the healed wound is barely distinguishable from the surrounding tissue.

Figure 2C:
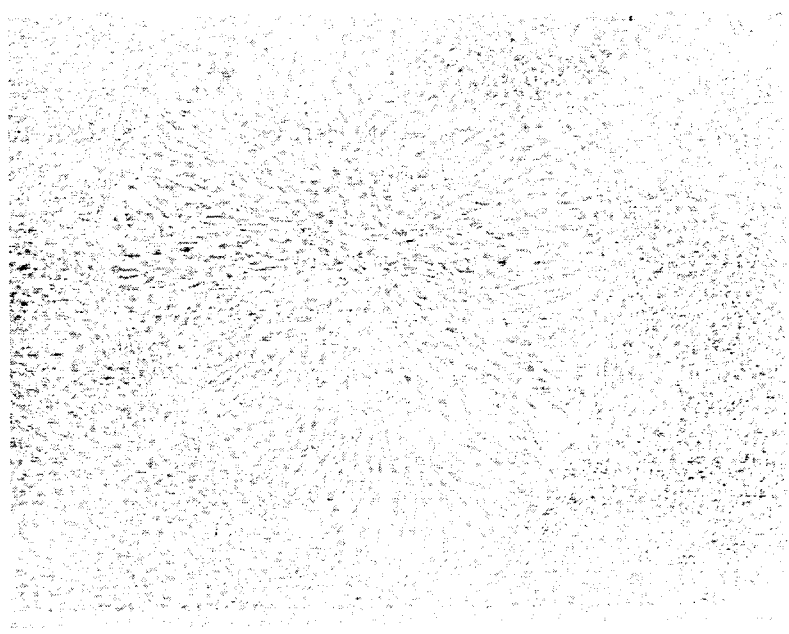
FIG. 2C is a phase micrograph of a wound in TM cultures containing 1 ug/ml 5-FU after 36 hours (original magnification × 82).

At 24 hours, TM cultures containing 1 ug/ml 5-FU showed radial migration of elongated cells toward the center of the wound (FIG. 2A). Adjacent fibers appear to be parallel. Complete healing was observed at 36 hours (FIG. 2C). The healed wound was clearly distinguishable from surrounding cells.

Figure 3A:
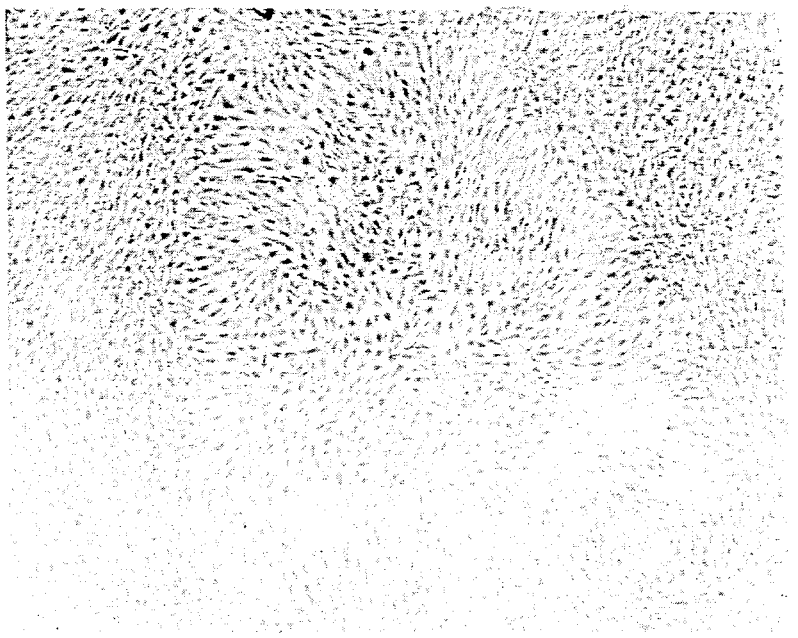
FIG. 3A is a phase micrograph of a wound in TM cultures containing 0.2 ug/ml 5-FU after 36 hours (original magnification × 80).
Figure 3B:
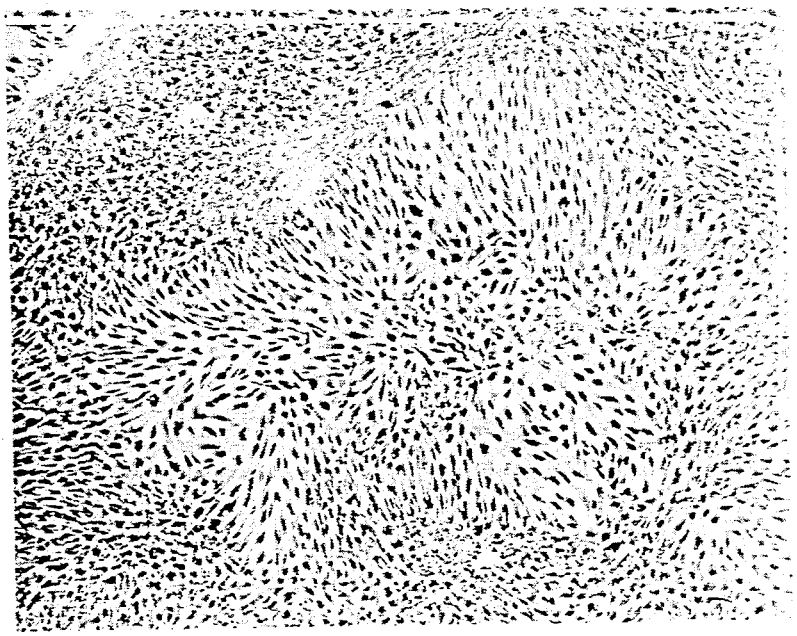
FIG. 3B is a phase micrograph of a wound in TM cultures with 5 ug/ml 5-FU after 36 hours (original magnification × 80).
Figure 4:
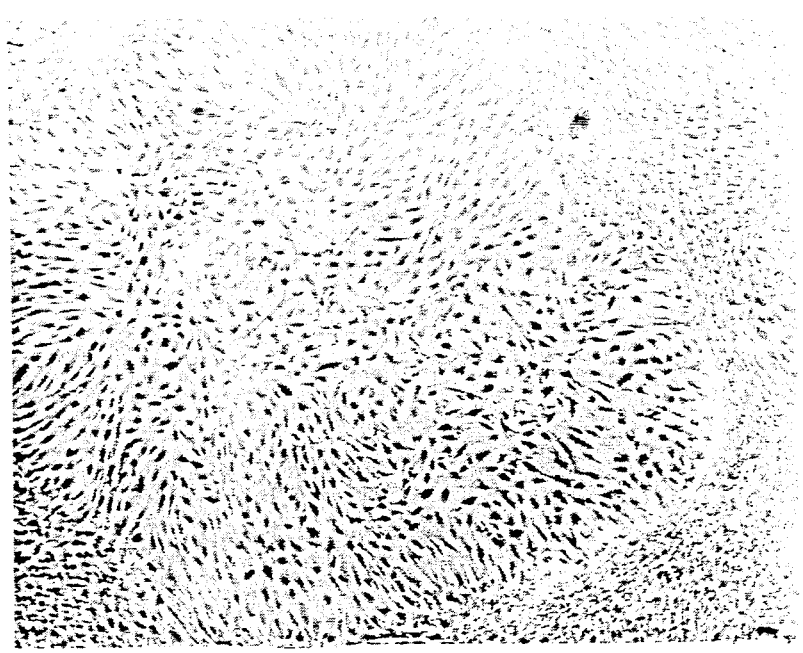
FIG. 4 is a phase micrograph of a wound in TM cultures containing 10 ug/ml 5-FU after 48 hours (original magnification × 100).
Figure 6B:
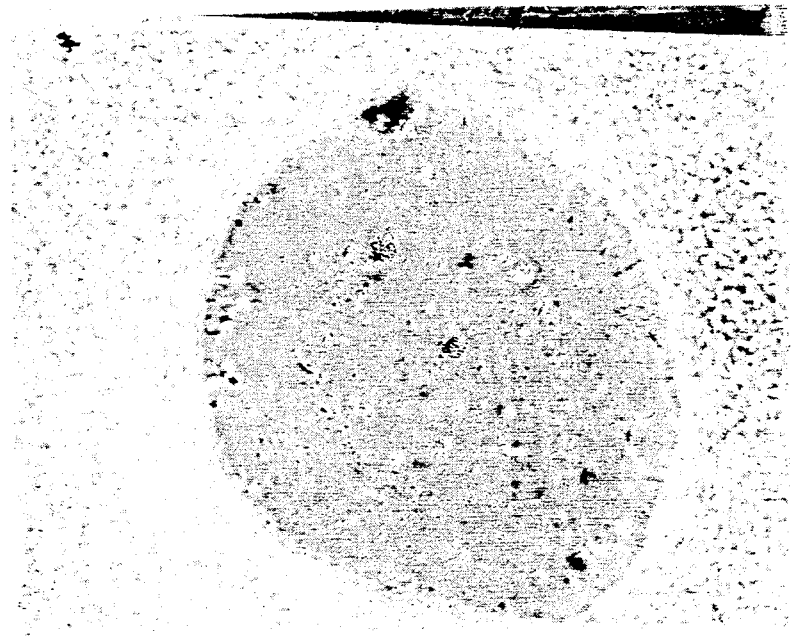
FIG. 6B is a phase micrograph of a wound in TM cultures in serum-free medium containing 15 ug/ml 5-FU after 48 hours (original magnification × 80).
Figure 6A:
FIG. 6A is a phase micrograph of a wound in TM cultures containing 15 ug/ml 5-FU after 48 hours (original magnification × 86).

In the range of 0.1 to 5 ug/ml, there seemed little difference in the action of the 5-FU (FIGS. 3A and 3B). At 10 ug/ml, the healing is comparable to control cultures except for cell alignment (FIG. 4). At 15 ug/ml, the 5-FU exhibited a clearly inhibiting action on the growth of TM cultures (FIG. 6A), especially in serum free medium (FIG. 6B).

Results with 5-FU treatment were different, and cell growth was faster compared to corresponding controls.

Figure 5:
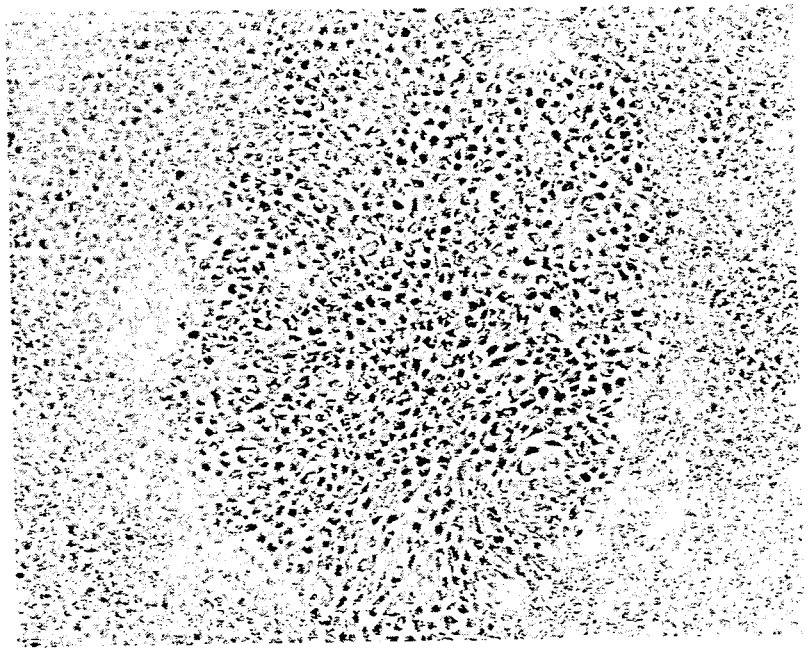
FIG. 5 is a phase micrograph of a wound in TM cultures initially exposed to 1 ug/ml 5-FU for 2 days; picture taken after 9 days exposure to 5-FU free medium (original magnification × 80).

Cultures of trabecular meshwork cells with continuing exposure to 5-FU retained a bundle shape pattern in the resurfacing area during long term studies. However, 5-FU cultures in which the healed wound was then exposed to 5-FU free medium exhibited a gradual change in the resurfacing cells (FIG. 5). After 10 to 15 days, the wound edge of the 5-FU free controls was no longer distinguishable.

Figure 7D:
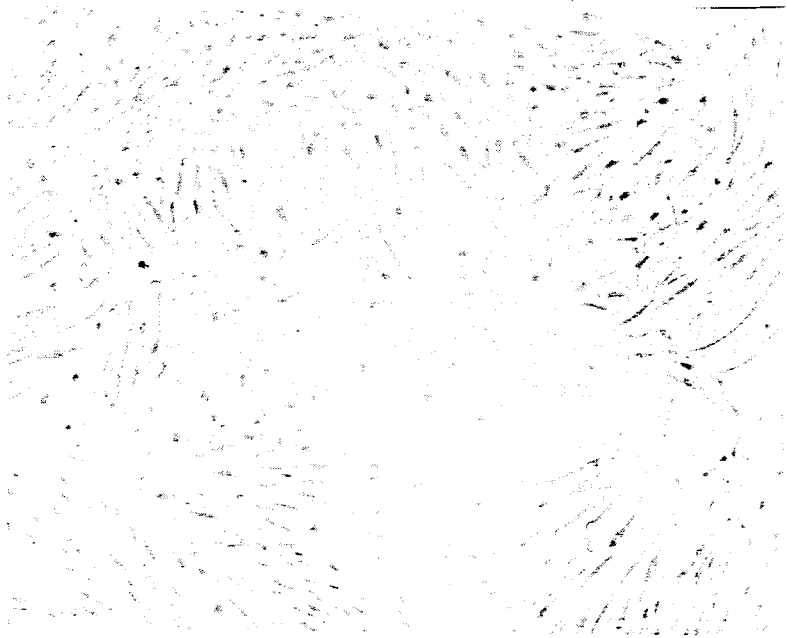
FIG. 7D is a phase micrograph of a wound in human fibroblast cultures treated with 10 ug/ml 5-FU after 24 hours (original magnification × 80).
Figure 7C:
FIG. 7C is a phase micrograph of a wound in a wound in human fibroblast cultures treated with 0.5 ug/ml 5-FU after 24 hours (original magnification × 86).

Addition of 0.1 to 10 ug/ml 5-FU medium to human Fibroblast cultures produced no change in healing time or alteration of visible cell structure (FIGS. 7C and 7D).

IMMUNOSTAINED CULTURES

TM Cytoskeletal Structures

After fixing and staining, cytoskeletal structures were studied under the Fluorescent microscope.

Figure 8:
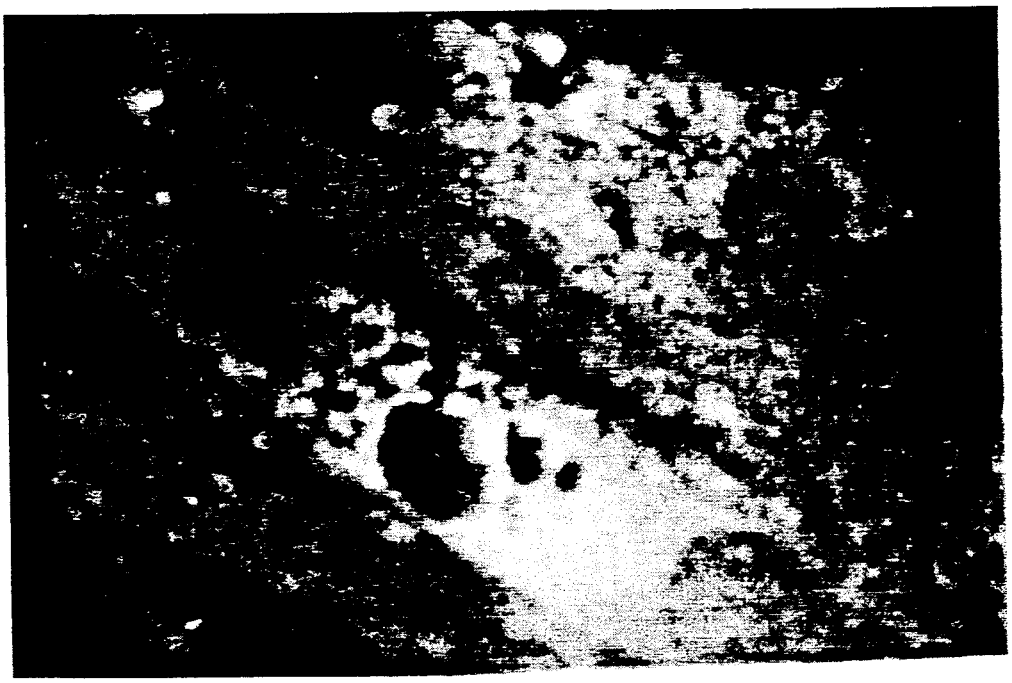
FIG. 8 is cytoskeletal study of formaldehyde fixed cells in unpermeablized both control and 5-FU cultures, with greater intensity in the perinuclear area in the 5-FU treated cultures (original magnification × 2520).

A cytoskeletal study of fixed unpermeablized TM cells shows a greater intensity of material in the perinuclear area in 5-FU treated cultures (FIG. 8).

Figure 9B:
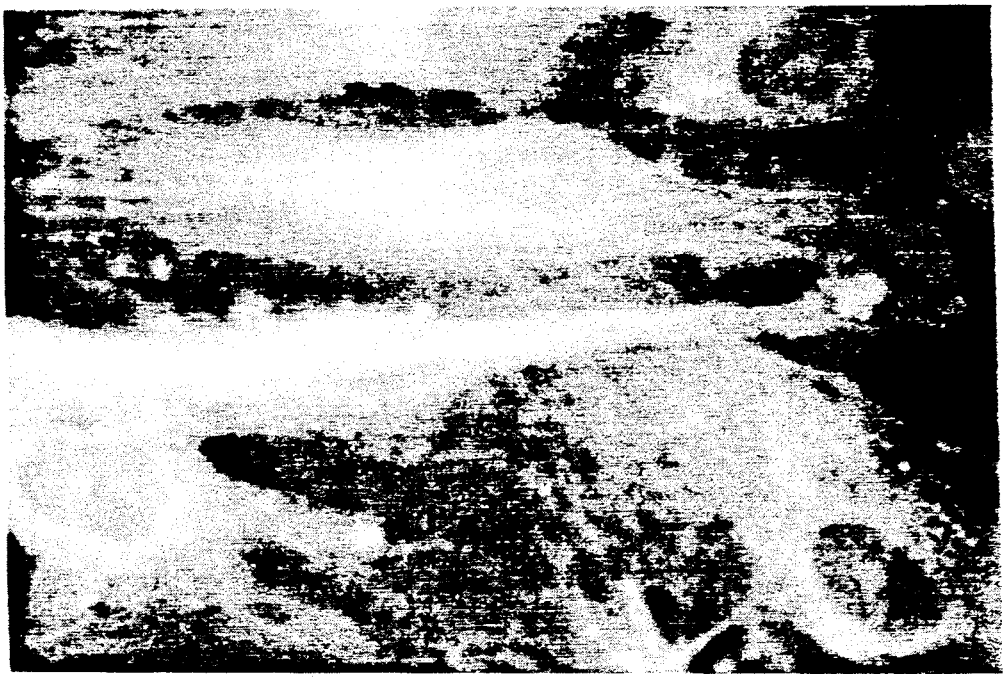
FIG. 9B shows staining for action microfilaments of TM cells in 5-FU (1 ug/ml) treated cultures (original magnification × 3150).
Figure 9A:
FIG. 9A shows staining for actin microfilaments of TM control cells (original magnification × 3150).

Immunostaining of TM cultures for actin microfilaments reveals stress fiber images which were observed throughout the cell body in parallel patterns (FIG. 9A). Deposition of material around the perinuclear area is observed in 5-FU treated cultures (FIG. 9B).

Figure 11B:
FIG. 11B shows immunostaining with anti-spectrin Ab of unpermeablized TM cells in 5-FU treated cultures (original magnification × 2520).
Figure 11A:
FIG. 11A shows immunostaining with anti-spectrin Ab of TM control cells (original magnification × 2520).
Figure 11D:
FIG. 11D shows a second view of immunostaining with anti-spectrin Ab of permeablized TM cells in 5-FU treated cultures (original magnification × 1575).
Figure 11C:
FIG. 11C shows a first view of immunostaining with anti-spectrin Ab of permeablized TM cells in 5-FU treated cultures (original magnification × 2520).

Immunostaining for spectrin in TM cultures not treated with 5-FU show proteins stained throughout the cell and well defined borders (FIG. 11A). Unpermeablized 5-FU treated cultures show honeycombing of fibers at the perinuclear area and a poorly defined cell border (FIG. 11B). Permeablized 5-FU treated cultures show multilayers of fibers with honeycombing throughout the cell (FIG. 11C) and several thick fiber bridges between cells (FIG. 11D).

Figure 10B:
FIG. 10B shows staining for vimentin intermediate filaments of TM cells in 5-FU treated cultures (original magnification × 3150).
Figure 10A:
FIG. 10A shows staining for vimentin intermediate filaments of TM control cells (original magnification × 3239).
Figure 10C:
FIG. 10C shows staining for vimentin intermediate filaments of TM cells in 5-FU treated cultures with vacuoles indicated by arrows (original magnification × 3150).

Immunostaining for vimentin in TM cultures not treated with 5-FU shows a filamentous pattern radiating from near the nucleus to the cell periphery (FIG. 10A). In cultures treated with 5-FU deposition of material is observed at the perinuclear area as well as along fibers at the cell borders (FIG. 10B). Fibers appear thicker with several vacuoles evident around the nucleus (FIG. 10C).

Immunostaining of TM cultures for alpha-actin, desmin, filamin and tubulin showed no marked differences between treated and untreated cultures.

TM Extracellular Structures

Figure 13B:
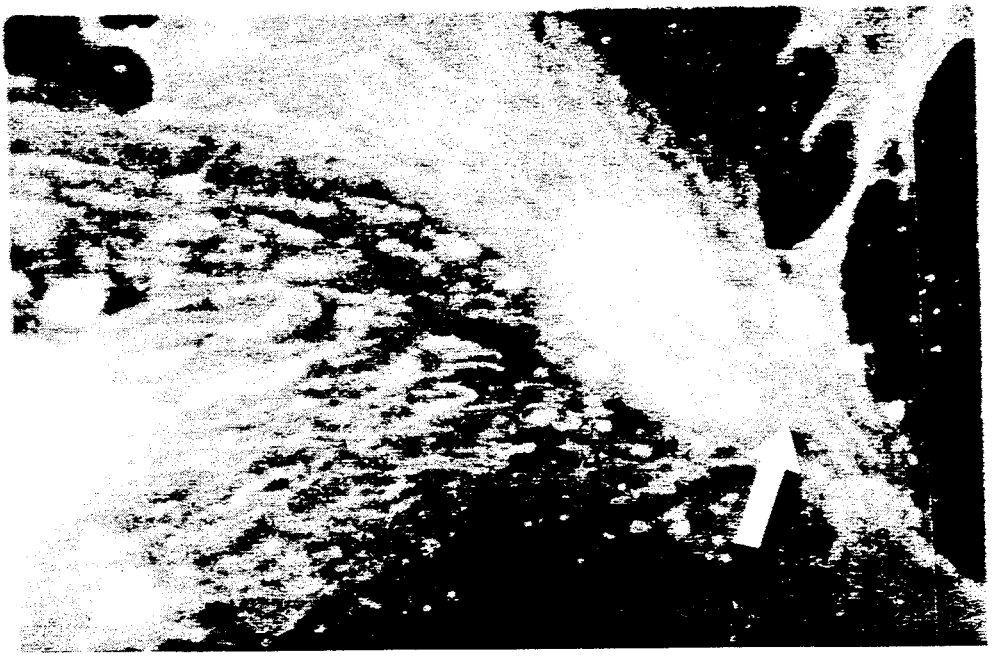
FIG. 13B shows staining for collagen of wounded area TM cells in 5-FU treated cultures with an arrow indicating the location of vacuole and granules (original magnification × 2600).
Figure 13A:
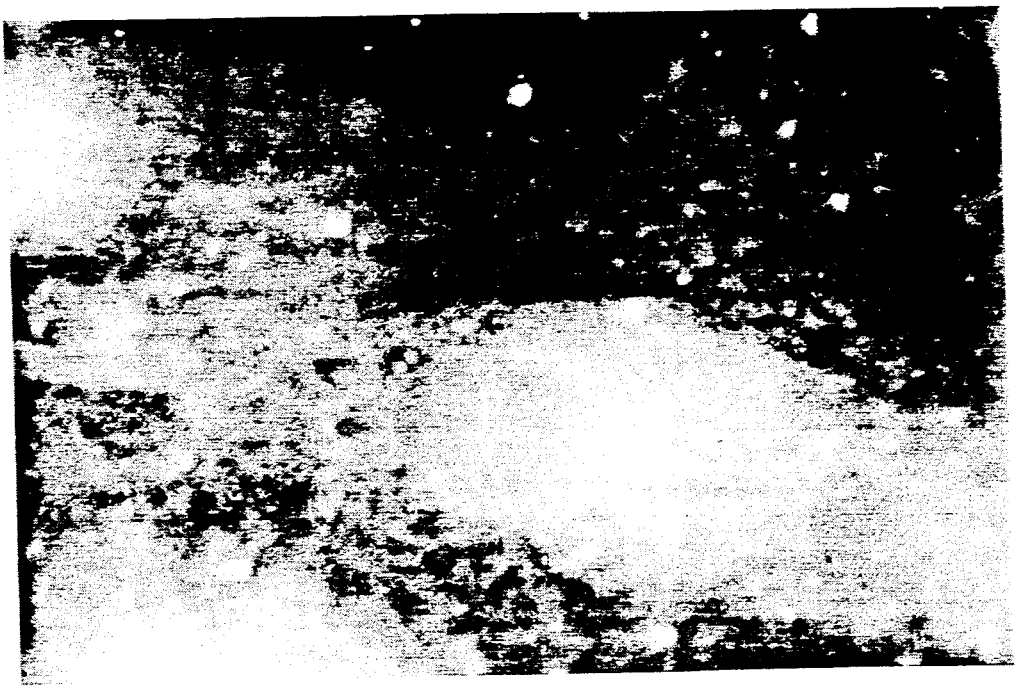
FIG. 13A shows staining for collagen after fixation and staining of TM control cells (original magnification × 3150).

Immunostaining for collagen in permeablized TM cell cultures samples not treated with 5-FU show general staining. Fibers are not clearly defined and no residue is observed around the nucleus (FIG. 13A). In cultures treated with 5-FU, fibers are clearly defined and had attached granules in cells in the resurfaced area. The granulated fibers extended from near the nucleus to the peripheral regions of the cell (FIG. 13 B). Some vacuoles are observed in the perinuclear area. For cells in the confluent area, fibers are not clearly defined, few granules are observed and perinuclear regions contain less vacuoles.

Figure 15B:
FIG. 15B shows staining for fibronectin of permeablized TM cells in 5-FU treated cultures with arrows indicating thick staining along borders (original magnification ×6300).
Figure 15A:
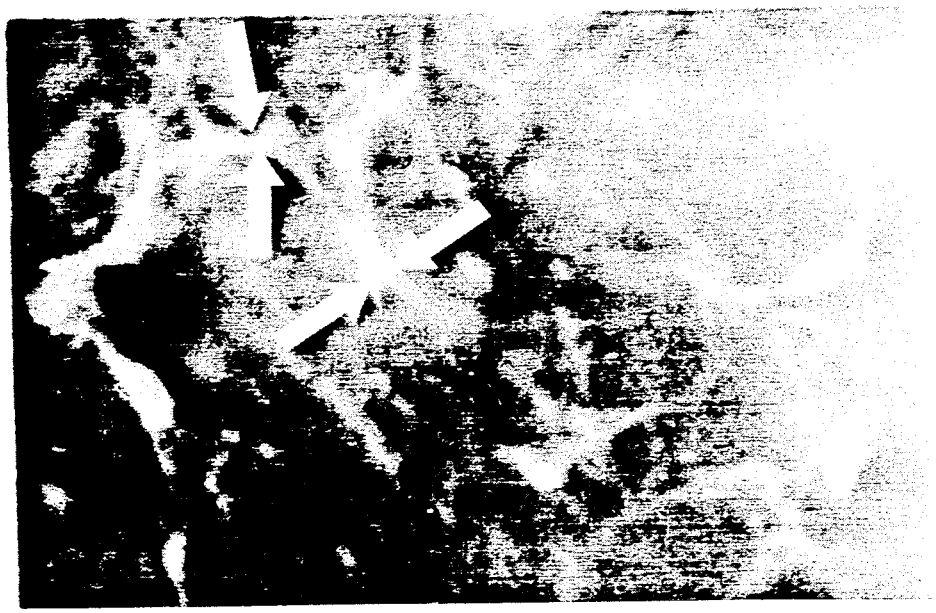
FIG. 15A shows staining for fibronectin of TM control cells with arrows indicating thin staining along cell borders (original magnification ×6300).
Figure 15D:
FIG. 15D shows staining for fibronectin of TM cells in 5-FU treated cultures with accumulation of migrated fibers between cells (original magnification ×3780).
Figure 15C:
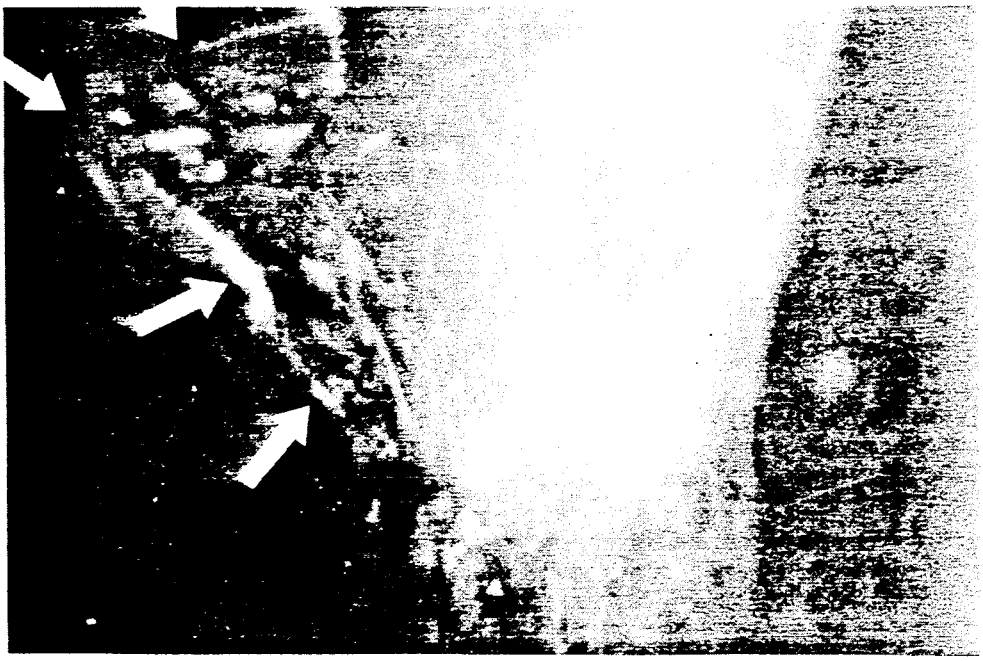
FIG. 15C shows staining for fibronectin of TM cells in 5-FU treated cultures with migration of granulated stress fibers along other fibers from the perinuclear region toward the extreme borders of the cells indicated by arrows (original magnification ×2520).
Figure 15E:
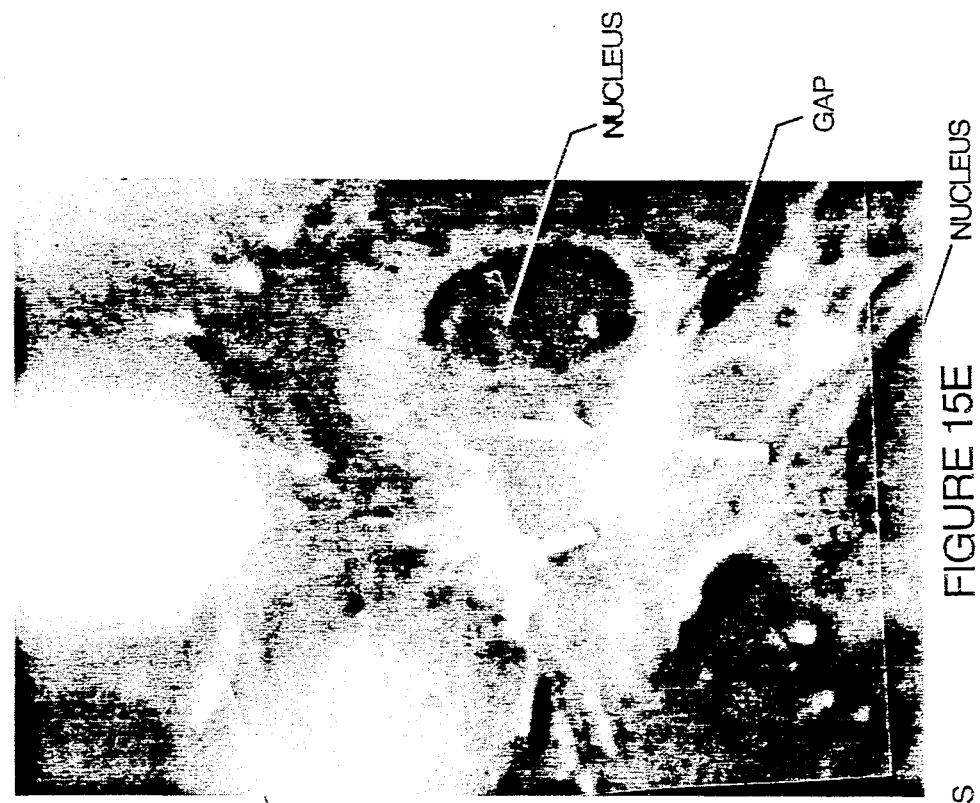
FIG. 15E shows staining for fibronectin of TM cells in the wounded area of 5-FU treated cultures with an accumulation of thick stress fibers filling a gap between cells indicated by arrows (original magnification ×3780).
Figure 15F:
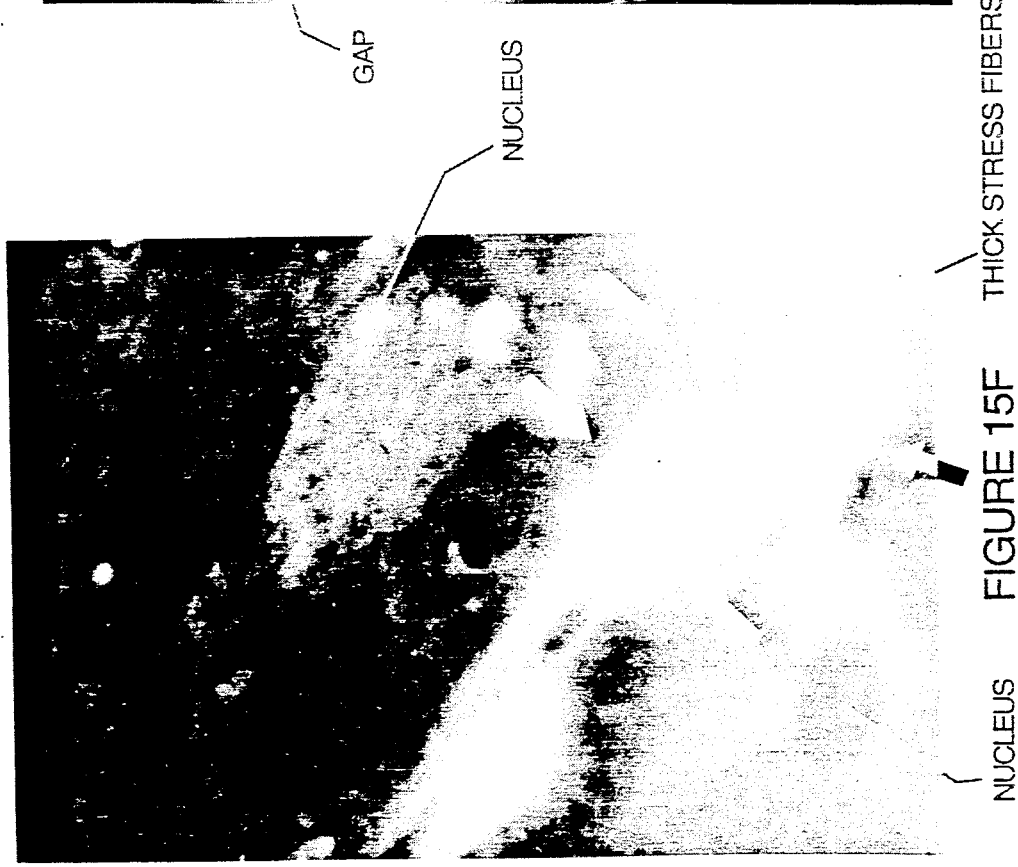
FIG. 15F shows staining for fibronectin of TM cells in 5-FU treated cultures with accumulation of thick stress fibers indicated by arrows (original magnification ×3150).
Figure 15G:
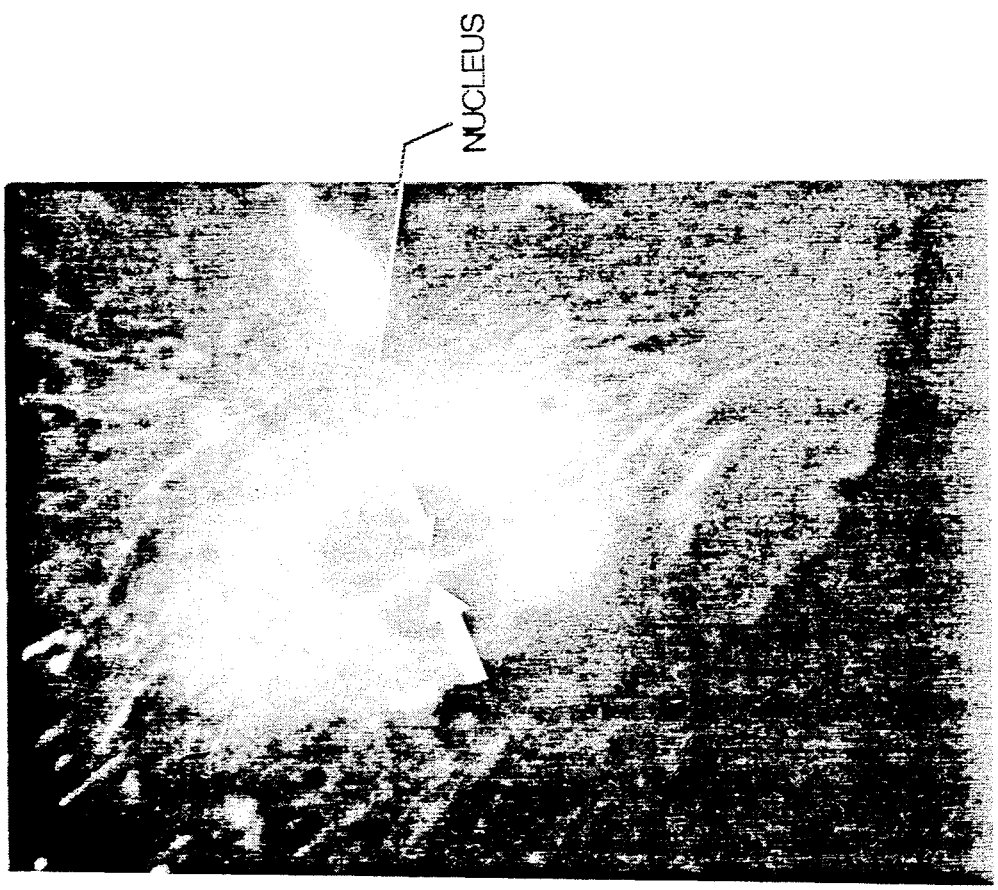
FIG. 15G shows staining for fibronectin of TM cells in 5-FU treated cultures with accumulation of stress fibers overlapping the nucleus is indicated by arrows (original magnification ×3000).

Immunostaining for fibronectin in TM cell cultures not treated with 5-FU shows thin staining along the cell borders (FIG. 15A). In cultures treated with 5-FU, heavy staining is observed along cell borders (FIG. 15B). Migration of fibers having attached granules is observed along other fibers from the perinuclear region toward the borders of the cells (FIG. 15C). A graduated accumulation of these migrated fibers is observed between cells in the extracellular matrix (FIG. 15D). Accumulation of these fibers filled gaps between cells in the resurfaced area and is observed as thick stress fibers (FIG. 15E), some of which span the nucleus (FIG. 15G), and accumulate between cells where a gap exists (FIG. 15F). Fibronectin is an elongated cell surface protein which enables cells to interact with the extracellular matrix. Each domain of fibronectin can specifically bond to certain protein molecules outside the cell such as fibrin, collagen and heparin. This protein is important for cell migration, development and wound healing.

Immunostaining for laminin in TM cell cultures shows an increase in staining around the nucleus in cultures treated with 5-FU.

Fibroblast cells

Figure 12:
FIG. 12 shows immunostaining with anti-spectrin Ab in human fibroblast cells treated with 5-FU (original magnification × 3780).

Immunostaining for actin, alpha-actin, desmin, filamin, tubulin, and vimentin and immunostaining of 5-FU treated cultures does not appear markedly different from controls. The fibroblast cells appear spindle shaped with a prominent nucleus. Immunostaining for spectrin shows no extra fibers vacuoles or deposits around the nucleus or cell body (FIG. 12).

Figure 14B:
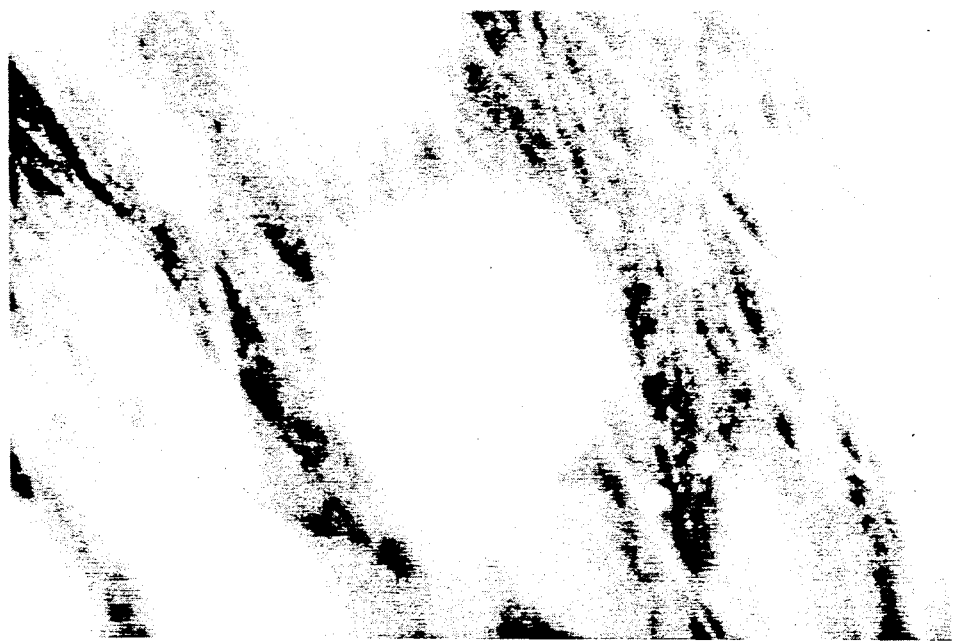
FIG. 14B shows staining for collagen in 5-FU treated fibroblast cells (original magnification × 2520).
Figure 14A:
FIG. 14A shows staining for collagen in control fibroblast cells (original magnification × 3150).

Immunostaining for collagen in control fibroblast cells shows spindle shaped cells with fibers radiating from the cell to every direction (FIG. 14A). Fibroblast cultures containing 5-FU are nonspecific and only show staining around the nucleus (FIG. 14B).

Figure 16B:
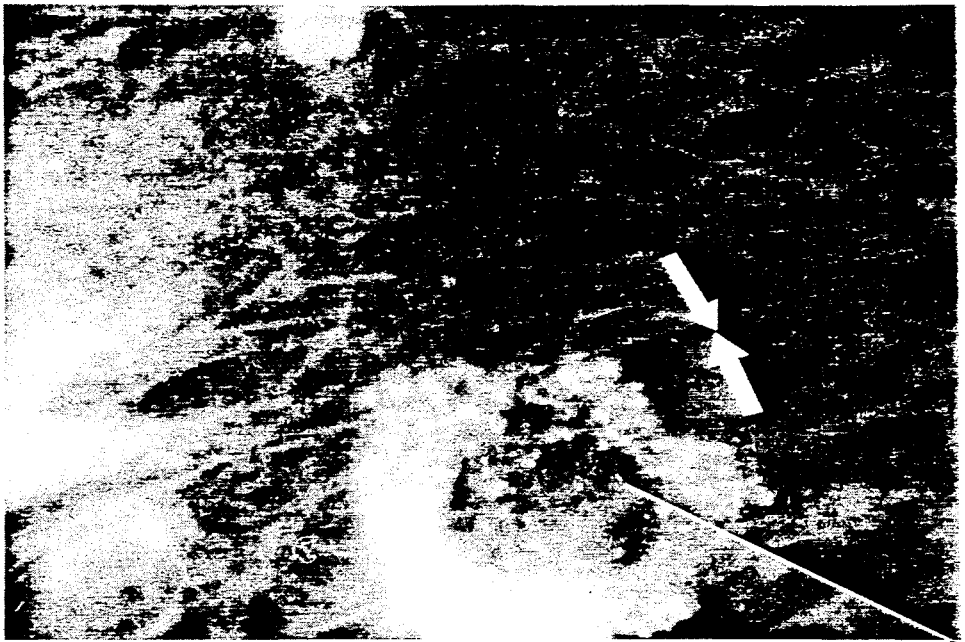
FIG. 16B shows staining for fibronectin of fibroblast cells in 5-FU treated cultures with arrows indicating thin staining along borders (original magnification ×3780).
Figure 16A:
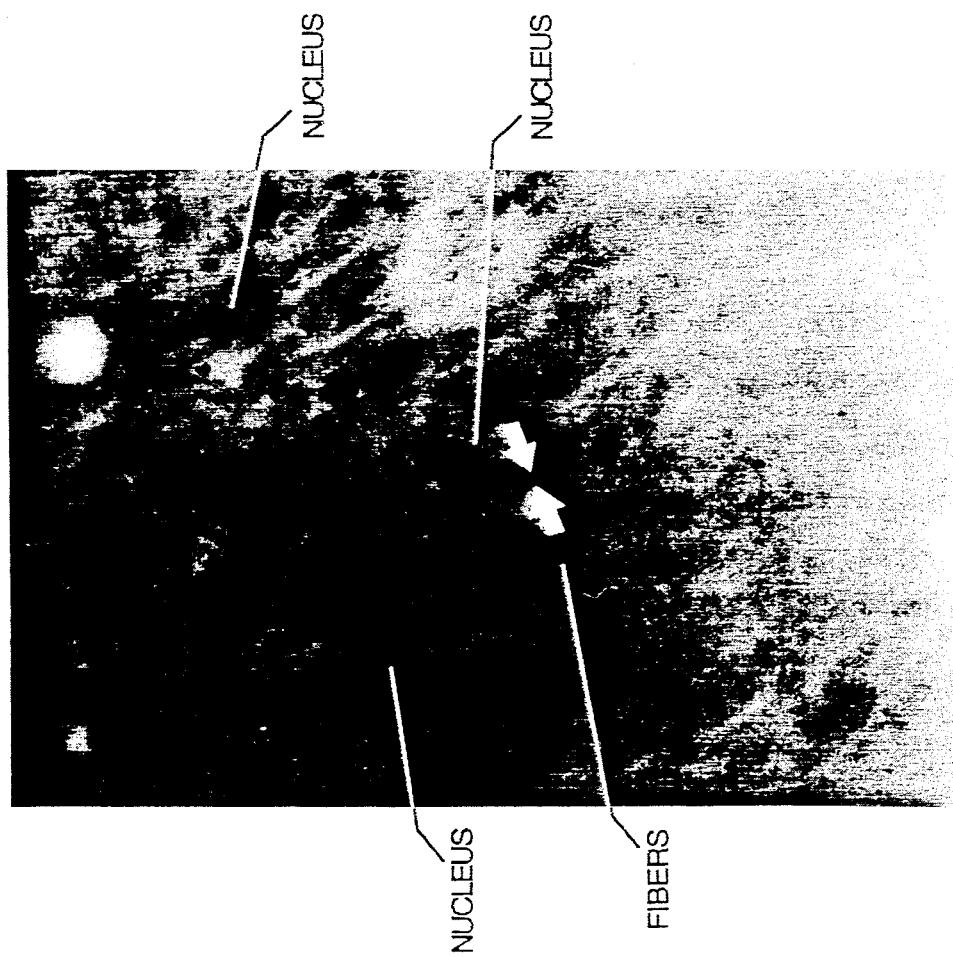
FIG. 16A shows staining for fibronectin of fibroblast control cells with arrows indicating indistinct fibers (original magnification ×6300).

Fibronectin immunostaining in control fibroblast cells shows nondistinct fibers in the extracellular matrix (FIG. 16A). Perinuclear staining is obvious in cultures containing 5-FU. Very thin stress fibers are observed in the extracellular matrix. No overlapping of fiber nor any granules are observed (FIG. 16B).

Summary of the Invention

Adding 5-FU between 0.1 and 10 ug/ml, stimulates cell migration in TM cell cultures. Adding more than 10 ug/ml to TM cell cultures inhibits cell migration into the wound. The stimulated, migrating TM cells show a specific bundle shaped morphology radiating from the edge of the wound toward the center. These enlongated cells contain a lower ratio of nucleus to cytoplasm and more fibers than untreated TM cells. Immunostaining shows these fibers contain mostly actin, spectrin and vimentin fibers. There is also an increased number of vacuoles around the nucleus of 5-FU treated TM cells. The monolayer of cells appears to be multilayered due to excess fibers and/or attached granules along the fibers forming a 3-dimensional matrix. The extracellular matrix shows changes, like granule formation on collagen and fibronectin fibers. Fibronectin fibers accumulate along cell borders, subsequently filling gaps between cells. The elongation of the cells is reversible upon removal of 5-FU from the medium.

It is believed that application of 5-FU in a dose which results in a cellular concentration of less than 10 ug/ml could stimulate the TM cells and cover denuded areas occurring in glaucoma, improving filtration of the aqueous humor by these cells, and subsequently could increase drainage by the Schlemm's canal. A dose of between 0.1–2 ug/ml give as a drop, or subconjunctival injection is proposed. Alternatively, the dose could be delivered by any known method such as a ointment or implant.

Use of prodrugs such as 1-Alkoxy-Corbonyl 5-FU can drastically increase lipophilic properties of 5-FU and resultant corneal penetration. The inventor suggests that use of prodrugs might enhance the effect of 5-FU on TM cells and further reduce the dosage of the drug needed for stimulation of the TM cells.

It is further proposed that although fibroblasts do not show resurfacing enhancements as a result of exposure to 5-FU, cells other than trabecular meshwork cells might be responsive to such treatment. Of special interest would be spleen cells (treatment of ruptured spleen), nerve cells (treatment of severe nerve damage like Parkinsons and Alzheimers), and glandular cells (treatment of Diabetes).

It is also proposed that although colchicine does not enhance resurfacing by TM cells that other antimitotic agents may be determined which do enhance migration of TM or other cells.

Available growth factors (from ICN or SIGMA) include B-cell, colony stimulating, endothelial, epidermal, erythropoietin, ewing sarcoma, fibroblast, liver cell, hybridoma, insulin-like, interleukin, keratinocyte, lactoferrin, nerve, platelet derived, transforming, and tumor necrosis factors. Combining 5-FU and growth factors could be useful in tissue repair.

It is also possible that growth in plant cells could likewise be stimulated to encourage migration while suspending mitosis, and agricultural applications of this technique be developed either by use of antimetabolites such as 5-FU alone or in combination with plant growth regulating substances such as auxins.

Studies should be done on animals for confirmation of the effect of 5-FU on TM cells in vivo. If studies confirm the result of the in vitro examples, a new way to treat glaucoma by resurfacing areas damaged by aging and decreased resistance to outflow would be available.

What is claimed is:

1. A method for stimulating healing of a damaged group of trabecular meshwork cells comprising the step of:
    exposing said cells to a dosage of an antimitotic, said dosage being in a concentration low enough to stimulate healing of said cells.

2. The method of claim 1 wherein said antimitotic is a halouracil.

3. The method of claim 2 wherein said halouracil is 5-fluorouracil.

4. The method of claim 3 wherein said concentration is less than 10 ug/ml.

5. The method of claim 2 further comprising the step of ceasing said exposure.

6. The method of claim 5 further comprising the step of enriching the supply of native bases to said cells.

7. The method of claim 6 wherein said bases are chosen from the group consisting of thymine and uracil.

8. The method of claim 2 further comprising the step of: exposing said cells to an adjuvant, said adjuvant chosen from the group consisting of prodrugs and growth factors, such that the effect of said halouracil is enhanced.

9. A method for stimulating healing of damaged cells comprising:
    exposing said cells to a dosage of an antimitotic, said dosage being in a concentration low enough to stimulate migration of said cells.

* * * * *